US012120099B2

(12) United States Patent
Manicka

(10) Patent No.: US 12,120,099 B2
(45) Date of Patent: Oct. 15, 2024

(54) SECURE COMMUNICATIONS BETWEEN AN IMPLANTABLE BIOMEDICAL DEVICE AND AUTHORIZED PARTIES OVER THE INTERNET

(71) Applicant: Manicka Institute LLC, Woodbury, MN (US)

(72) Inventor: Yatheendhar D. Manicka, Woodbury, MN (US)

(73) Assignee: MANICKA INSTITUTE LLC, Woodbury, MN (US)

( * ) Notice: Subject to any disclaimer, the term of this patent is extended or adjusted under 35 U.S.C. 154(b) by 506 days.

(21) Appl. No.: 17/105,421

(22) Filed: Nov. 25, 2020

(65) Prior Publication Data

US 2022/0161038 A1    May 26, 2022

(51) Int. Cl.
*H04L 9/40* (2022.01)
*A61N 1/372* (2006.01)
(Continued)

(52) U.S. Cl.
CPC ...... *H04L 63/0442* (2013.01); *A61N 1/37254* (2017.08); *A61N 1/37282* (2013.01);
(Continued)

(58) Field of Classification Search
CPC .......... H04L 63/0442; H04L 63/0492; H04W 12/06; H04W 12/50; H04W 12/63; A61N 1/37254; A61N 1/37282; G16H 40/67
See application file for complete search history.

(56) References Cited

U.S. PATENT DOCUMENTS 6,358,202 B1   3/2002  Arent
6,442,432 B2   8/2002  Lee
(Continued)

FOREIGN PATENT DOCUMENTS

EP    1241982 B1    10/2006
EP    3091459 A1    11/2016

OTHER PUBLICATIONS

Belkhouja, Taja; Mohamed, Amr; Al-Ali, Abdulla K.; Du, Xiaojiang; Guizani, Mohsen; "Light-weight encryption of wireless communication for implantable medical devices using henon chaotic system (invited paper)," Int'l Conference on Wireless Networks and Mobile Communications (WINCOM), Rabat, Morocco, 2017, 6 pages.*
(Continued)

*Primary Examiner* — Victor Lesniewski
(74) *Attorney, Agent, or Firm* — Kinney & Lange, P.A.

(57) ABSTRACT

Apparatus and associated methods relate to facilitating a remote internet-connected device to configure an implantable biomedical device. Such configuration of the implantable biomedical device involves hosting a virtual image of the implantable biomedical device at an IP-addressable internet site associated therewith. This virtual image is updated based on configuration data received from the remote internet-connected device via the internet. configuration data for the implantable biomedical device at the IP-addressable internet site. The safety of such an updated implantable medical device is validated based on the updated virtual image. The configuration data is then transmitted from the IP-addressable internet site via the internet to the implantable biomedical device, in response to the safety of the implantable biomedical device being validated.

16 Claims, 5 Drawing Sheets

(51) Int. Cl.
*G16H 40/67* (2018.01)
*H04W 12/06* (2021.01)
*H04W 12/50* (2021.01)
*H04W 12/63* (2021.01)

(52) U.S. Cl.
CPC ......... *G16H 40/67* (2018.01); *H04L 63/0492* (2013.01); *H04W 12/06* (2013.01); *H04W 12/50* (2021.01); *H04W 12/63* (2021.01)

(56) References Cited

U.S. PATENT DOCUMENTS

| | | | |
|---|---|---|---|
| 6,622,050 | B2 | 9/2003 | Thompson |
| 6,735,478 | B1 | 5/2004 | Snell |
| 6,804,558 | B2 | 10/2004 | Haller et al. |
| 7,009,511 | B2 | 3/2006 | Mazar et al. |
| 7,065,409 | B2 | 6/2006 | Mazar |
| 7,127,300 | B2 | 10/2006 | Mazar et al. |
| 7,149,773 | B2 | 12/2006 | Haller et al. |
| 7,181,505 | B2 | 2/2007 | Haller et al. |
| 7,198,603 | B2 | 4/2007 | Penner et al. |
| 7,225,030 | B2 | 5/2007 | Kroll et al. |
| 7,292,139 | B2 | 11/2007 | Mazar et al. |
| 7,395,117 | B2 | 7/2008 | Mazar et al. |
| 7,908,334 | B2 | 3/2011 | Huelskamp et al. |
| 8,078,278 | B2 | 12/2011 | Penner |
| 8,685,091 | B2 | 4/2014 | Caylor, III |
| 8,700,172 | B2 | 4/2014 | Mazar et al. |
| 9,114,265 | B2 | 8/2015 | Mazar et al. |
| 9,215,075 | B1 | 12/2015 | Poltorak |
| 9,578,449 | B2 | 2/2017 | Mazar et al. |
| 9,942,051 | B1 | 4/2018 | Poltorak |
| 9,979,810 | B2 | 5/2018 | Mazar et al. |
| 10,305,695 | B1 | 5/2019 | Poltorak |
| 2002/0059049 | A1 | 5/2002 | Bradbury et al. |
| 2005/0159787 | A1 | 7/2005 | Linberg et al. |
| 2005/0240246 | A1* | 10/2005 | Lee ............... A61N 1/37282 607/30 |
| 2005/0283198 | A1* | 12/2005 | Haubrich ........ A61N 1/37282 607/30 |
| 2009/0054948 | A1* | 2/2009 | Webb ................. G16H 40/67 607/31 |
| 2009/0125084 | A1 | 5/2009 | Juels et al. |
| 2010/0010585 | A1* | 1/2010 | Davis ............... A61N 1/36132 607/62 |
| 2012/0197347 | A1* | 8/2012 | Olson ................. A61M 5/172 607/60 |
| 2013/0108046 | A1* | 5/2013 | Andersen ............ H04W 12/06 380/283 |
| 2015/0089590 | A1 | 3/2015 | Krishnan et al. |
| 2015/0367136 | A1* | 12/2015 | Rondoni ........... A61N 1/37252 607/42 |
| 2016/0156599 | A1 | 6/2016 | Son et al. |
| 2016/0235301 | A1 | 8/2016 | Melodia et al. |
| 2016/0330573 | A1 | 11/2016 | Masoud et al. |
| 2016/0374124 | A1* | 12/2016 | Gothe ............... A61N 1/37217 |
| 2017/0111488 | A1 | 4/2017 | Mazar et al. |
| 2017/0196458 | A1 | 7/2017 | Ternes et al. |
| 2017/0259072 | A1 | 9/2017 | Newham et al. |
| 2017/0279571 | A1 | 9/2017 | Melodia et al. |
| 2018/0028827 | A1* | 2/2018 | Schilling ........... A61N 1/37223 |
| 2018/0302386 | A1 | 10/2018 | Childress et al. |
| 2019/0184108 | A1 | 6/2019 | Sjolund et al. |
| 2020/0093431 | A1 | 3/2020 | Bailey et al. |
| 2020/0139140 | A1 | 5/2020 | Crawford |
| 2021/0065906 | A1* | 3/2021 | Villongco ................ A61B 5/35 |
| 2021/0343017 | A1* | 11/2021 | Jordan .................. G06T 7/0016 |
| 2022/0035900 | A1* | 2/2022 | Flakne ............... A61N 1/37247 |
| 2022/0159468 | A1* | 5/2022 | Prutchi .................... H04B 5/79 |

OTHER PUBLICATIONS

Zheng, Guanglou; Fang, Gengfa; Shankaran, Rajan; Orgun, Mehmet A.; "Encryption for Implantable Medical Devices Using Modified One-Time Pads," IEEE Access, vol. 3, pp. 825-836, 2015.*
Extended European Search Report for European Patent Application No. 21275168.9, dated Apr. 22, 2022, 8 pages.
Extended European Search Report for European Patent Application No. 21275167.1, dated Mar. 24, 2022, 9 pages.
Extended European Search Report for European Patent Application No. 21275166.3, dated Apr. 19, 2022, 9 pages.
V.B. Kulkarni, "A doctor on World Wide Web: a biomedical wireless Internet application," 2002 IEEE International Conference on Personal Wireless Communications, 2002, pp. 182-186, doi: 10.1109/ICPWC.2002.1177273. (Year: 2002).
E. Hamadaqua, A. Abadleh, A. Mars and W. Adi, "Highly Secured Implantable Medical Devices," 2018 International Conference on Innovations In Information Technology (IIT), 2018, pp. 7-12, doi: 10.1109/INNOVATIONS.2018.8605968. (Year: 2018).
Griggs, Kristen N., et al. "Healthcare blockchain system using smart contracts for secure automated remote patient monitoring." Journal of medical systems 42.7 (2018): 1-7. (Year: 2018).
Communication pursuant to Article 94(3) for European Patent Application No. 21275168.9, dated Nov. 24, 2023, 4 pages.

* cited by examiner

SECURE COMMUNICATIONS BETWEEN AN IMPLANTABLE BIOMEDICAL DEVICE AND AUTHORIZED PARTIES OVER THE INTERNET

CROSS-REFERENCE TO RELATED APPLICATION(S)

This application is related to the following U.S. patent applications filed concurrently herewith: i) U.S. patent application Ser. No. 17/105,439, entitled "Antennas for a Subcutaneous Device," by Yatheendhar D. Manicka; ii) U.S. patent application Ser. No. 17/105,432, entitled "Secure Communications between an Implantable Biomedical Device and Authorized Parties over the Internet," by Yatheendhar D. Manicka; and iii) U.S. patent application Ser. No. 17/105,433, entitled "Secure Communications between an Implantable Biomedical Device and Authorized Parties over the Internet," by Yatheendhar D. Manicka. Each of the above cited and related U.S. patent applications are hereby incorporated by reference in its entirety.

BACKGROUND

Many different types of implantable biomedical devices are used to provide aid to patients for a variety of reasons. Some are used for mechanical purposes, such as, for example, joint replacements, lens replacements, stents, etc. Other implantable biomedical devices perform data operations, and therefore include electronic processing capabilities. Such "smart" implantable biomedical devices might monitor biological functions and/or provide therapies to the patient in whom the implantable biomedical device resides. For example, such "smart" implantable biomedical devices can include cardiac monitors, pacemakers, implantable cardioverter-defibrillators, and neural stimulators, etc. These implantable biomedical devices can sense biometrics of the body and use these biometrics for diagnostic or therapeutic purposes. For example, such implantable biomedical devices can deliver electrical stimulations and/or deliver drugs to the body for therapeutic purposes. For instance, a pacemaker can sense a heart rate of a patient, determine whether the heart is beating too fast or too slow, and transmit electrical stimulation to the heart to speed up or slow down different chambers of the heart. An implantable cardioverter-defibrillator can sense a heart rate of a patient, detect a dysrhythmia, and transmit an electrical shock to the patient so as to normalize the heart rate of the patient.

Such "smart" implantable biomedical devices can be configured to communicate sensed biometric data to the external world, as well as receive various data therefrom. Such data communications to and/or from an implantable biomedical device can present various risks. For example, sensed biometric data can contain information that is private to the patient, and therefore communications of such sensed biometric data should be secure so that only the intended authorized recipient is able to receive this sensitive data. Furthermore, configuration data sent to the "smart" implantable biomedical device can result in changes in the behavior and/or operation of the reconfigured device. Such changes should be prescribed only by authorized persons who are responsible for the care of the patient in whom the "smart" implantable biomedical device has been implanted. Such authorized persons might include, for example, the patient's physician and/or the manufacturer of the implantable biomedical device.

SUMMARY

Apparatus and associated methods relate to a method for facilitating a remote internet-connected device to configure an implantable biomedical device. The method includes hosting a virtual image of the implantable biomedical device at an IP-addressable internet site associated therewith. Then the method continues by receiving, by the IP-addressable internet site and from the remote internet-connected device via the internet, configuration data for the implantable biomedical device. The method then updates the virtual image hosted based on the configuration data received. Then the method validates safety of the implantable biomedical device based on the virtual image as updated. The method then transmits, from the IP-addressable internet site via the internet to the implantable biomedical device, the configuration data, in response to the safety of the implantable biomedical device being validated.

Some embodiments relate to a system for facilitating a remote internet-connected device to configure an implantable biomedical device. The system includes a hosting computer in communication with the internet and computer readable memory. The computer readable memory is encoded with instructions that cause the system to host a virtual image of the implantable biomedical device at an IP-addressable internet site associated therewith. The computer readable memory is further encoded with instructions that cause the system to receive, by the IP-addressable internet site and from the remote internet-connected device via the internet, configuration data for the implantable biomedical. The computer readable memory is further encoded with instructions that cause the system to update the virtual image hosted based on the configuration data received. The computer readable memory is further encoded with instructions that cause the system to validate safety of the implantable biomedical device based on the virtual image as updated. The computer readable memory is further encoded with instructions that cause the system to transmit, from the IP-addressable internet site via the internet to the implantable biomedical device, the configuration data, in response to the safety of the implantable biomedical device being validated.

DETAILED DESCRIPTION

Apparatus and associated methods relate to communications between an implantable biomedical device and various authorized entities via the internet. These apparatus and associated methods make secure communications between the implantable biomedical device and remote IP-addressable internet entities. Security for such communications to and/or from the implantable biomedical device are ensured via various security measures, such as, for example, proximal pairing, directional safety, and virtual mirroring of the implantable biomedical device. Communications between the implantable biomedical device and various of these authorized IP-addressable entities, such as a manufacturer of the implantable biomedical device or a physician of the patient in whom the implantable biomedical device has been implanted, can occur through a gatekeeping device—a paired proximate communications device, such as a cell phone of the patient, for example. Only if the gatekeeping device is proximate the implantable biomedical device, will some such communications be permitted. Furthermore, communications, such as updates or reconfigurations of the implantable biomedical device can be restricted to only those updates in which a direction of safety is increased for the patient (i.e., the implantable device will become more safe for the patient). Moreover, these updates and/or reconfigurations are performed first on a virtual device that mirrors the actual implantable biomedical device. Such updates and/or reconfigurations can be modeled and/or simulated so as to ensure increased safety of these changes to the implantable biomedical device. Security can be further strengthened using various additional methods, such as, for example, device authentication, and public-private security-key encoding, restrictions of some communications via intranets, virtual private networks, firewalls, etc.

Figure 1:
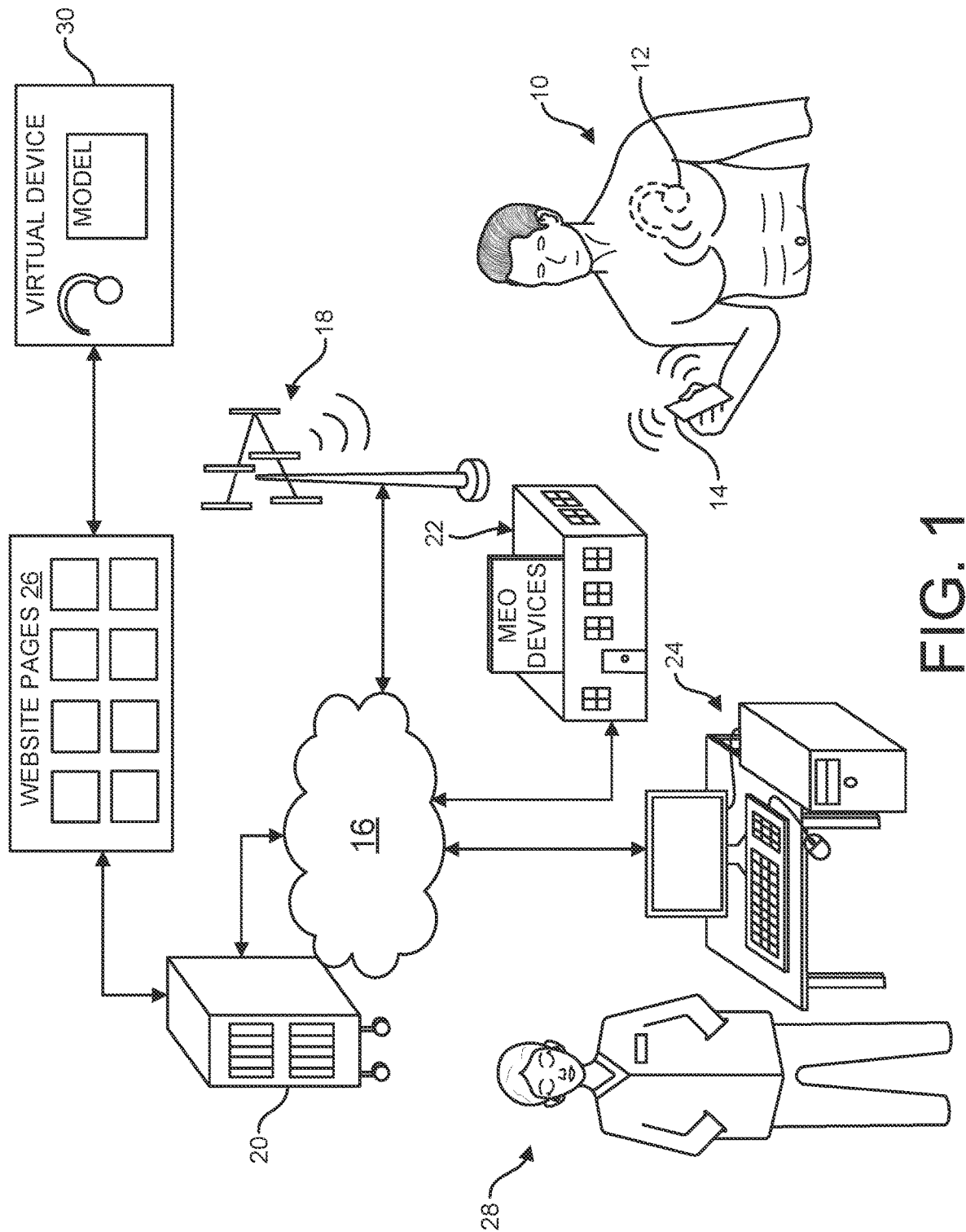
FIG. 1 is a schematic diagram depicting Internet Protocol (IP) based communications between an implantable biomedical device and a remote entity.

FIG. 1 is a schematic diagram depicting Internet Protocol (IP) based communications between an implantable biomedical device and a remote internet-based entity. In FIG. 1, patient 10 has implantable biomedical device 12 subcutaneously implanted within. Patient 10 is holding gatekeeping device 14 in his hand. In the depicted embodiment, gatekeeping device 14 is a smart phone, but gatekeeping device could be something different than a smartphone, such as, for example, a dedicated gatekeeping device specifically manufactured to perform such gatekeeping functions. Gatekeeping device 14 is depicted as facilitating communications between implantable biomedical device 12 and internet cloud 16. Because gatekeeping device 14 is a smart phone in the depicted embodiment, communications between internet cloud 16 and gatekeeping device 14 are transmitted via cell-phone tower 18. Gatekeeping device 14 is called such (i.e., "gatekeeping device") because gatekeeping device 14 operates as a gatekeeper for various communications between internet cloud 16 and implantable biomedical device 12. Myriad other devices and systems are configured to communicate with internet cloud 16, such as, for example, hosting server 20, medical device manufacturer 22, and personal computer 24. Hosting server 20 can be configured to host IP-addressable website 26 on the internet, for example. Personal computer 24 might be used by physician 26 of patient 10, for example.

IP-addressable website 26 includes virtual device 30 that is configured to precisely mirror implantable biomedical device 12, which had been implanted into patient 10. Hosting server 20 is configured to model or simulate the operation of implantable biomedical device 12 using virtual device 30. Such modeling can be performed so as to ensure safe operation of implantable medical device 12, before updates to and/or reconfigurations of actual implantable biomedical device 12 are performed. IP-addressable website 26 can have an IP address associated with the specific implantable biomedical device—implantable biomedical device 12—that has been implanted into patient 10. In some embodiment the IP address of IP-addressable website 26 is a static IP address that is secret (e.g., only known by a manufacturer, and perhaps the patient and/or physician). Implantable biomedical device 12 can also have a static IP address that is secret. The gatekeeping device can have either a static or a dynamic IP address, depending on the configuration of the gatekeeping device.

Because virtual device 30 is associated with implantable biomedical device 12, IP-addressable website 26 can appear as if it were implantable biomedical device 12 to those who have need to communicate with implantable biomedical device 12. For example, if physician 28 desires to update the configuration of implantable biomedical device 12 of patient 10, physician 28 can communicate such desired updated configuration to IP-addressable website 26, which is associated with implantable biomedical device 12. IP-addressable website 26 can then validate safety of such an updated and/or reconfigured implantable biomedical device 12 based on modeling and/or simulation of virtual device 30, before actually updating or reconfiguring implantable biomedical device 12 at a future time. Upon such validation of safety, IP-addressable website 26 can then transmit the configuration data to the actual implantable biomedical device 12 through gatekeeping device 14. In this way, it appears to physician 28 that when communicating with IP-addressable website 26, physician 28 is communicating with implantable biomedical device 12. Virtual device 30 will be described in more detail below in a section entitled: "Virtual Image (Mirrored Counterpart of Implantable Biomedical Device)."

Direction of safety for such updates and reconfigurations can be determined by IP-addressable website 26 based on the simulations of updated virtual device 30. If the direction of safety is improved (i.e., implantable biomedical device will operate in a manner that is more safe after the update or reconfiguration than before the update or reconfiguration) then the update or reconfiguration will be transmitted from IP-addressable website 26 to implantable biomedical device 12 (e.g., via gatekeeping device 14). If, however, the direction of safety is not improved (i.e., implantable biomedical device will operate in a manner that is not safer after the update or reconfiguration than before the update or reconfiguration) then the update or reconfiguration will not be transmitted by IP-addressable website 26. Directional safety will be described below in more detail below in a section entitled: "Directional Safety." Gatekeeping device 14 provides security to communications between implantable biomedical device 12 and internet cloud 16 via various methods and protocols. For example, gatekeeping device 14 has been paired with implantable biomedical device 12 at an earlier time. Biomedical device 12, for example, can be configured to ignore all attempted communications that are not originated by a device paired thereto, such as gatekeeping device 14. Secure pairing of one or few devices with implantable biomedical device 12 can prevent rogue communications from unauthorized devices. Furthermore, communications to and/or from implantable biomedical devices can be limited by a proximity requirement. For example, implantable biomedical device 12 can be configured to communicate only with devices that are within a predetermined range from implantable biomedical device 12. Methods for proximal limiting of communications to and/or from implantable biomedical device 12 will be described below.

In addition to using virtual device 30 and gatekeeping device 14, other security measures provide additional safety to communications between implantable biomedical device 12 and authorized persons. For example, data encryption between gatekeeping device and IP-addressable website 26 can be used to verify and/or validate the authorized source and destination of such communications, as well as preventing unwanted persons from decrypting such sensitive and/or private data. Authentication of authorized entities can also be performed so as to limit the number of entities that have authority to communicate with implantable biomedical device 12. Such gatekeeping security measures will be further described below in a section entitled: "Proximal Pairing."

Figure 2:
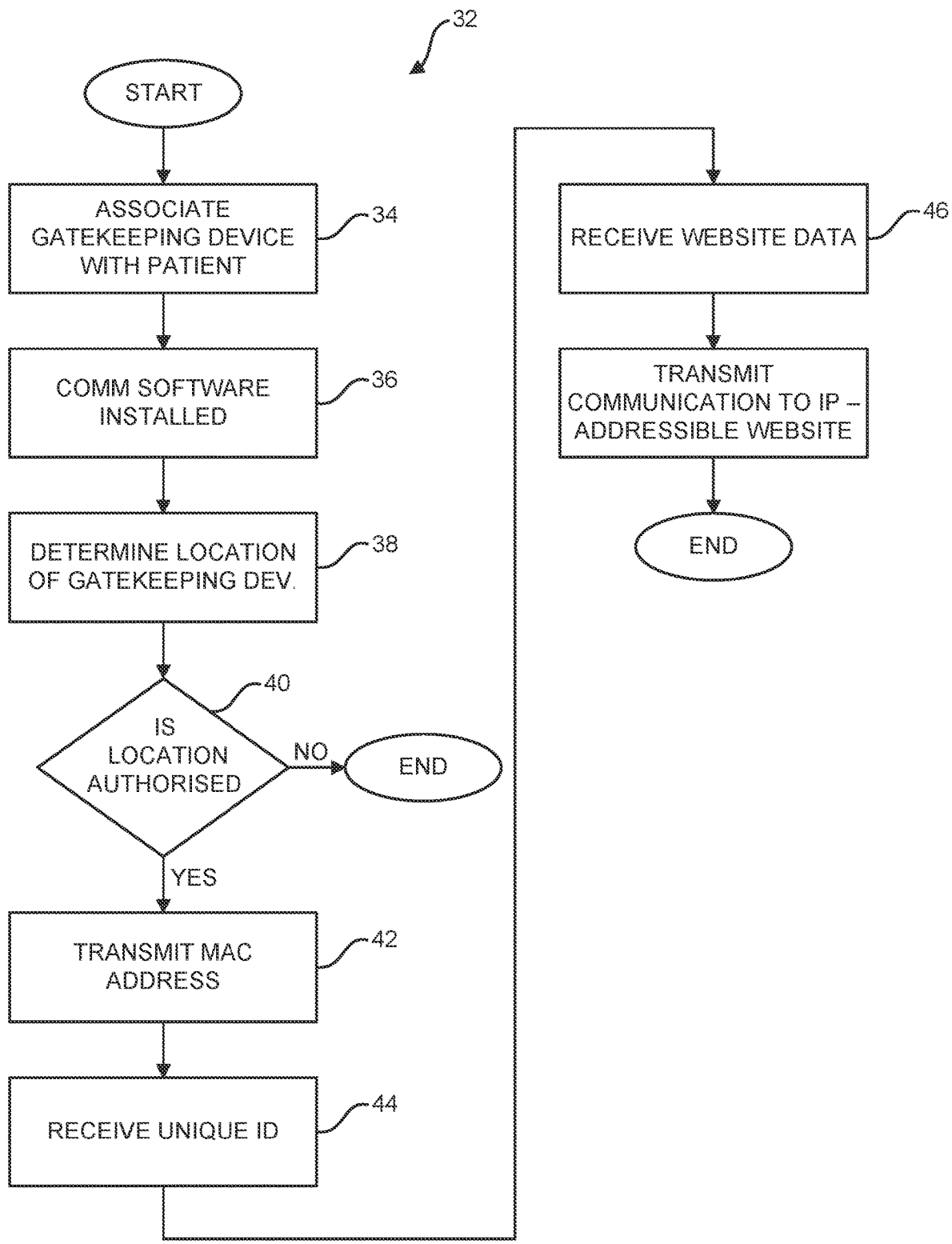
FIG. 2 is a flow chart of a method for secure pairing of a gatekeeping device with an implantable biomedical device.

FIG. 2 is a flow chart of a method for secure pairing of a gatekeeping device with an implantable biomedical device. In FIG. 2, method 32 is described from a vantage point of a processor of gatekeeping device 14 (depicted in FIG. 1). In some embodiments, method 32 will be performed at a time before or after implantable biomedical device 12 has been implanted into patient 10. Such secure pairing can be performed in a hospital where the implantation is performed, or at a physician's office after implantation has been performed, for example. Method 32 begins at step 34, where gatekeeping device 14 is associated with patient 10. Such association can include password or fingerprint protecting operation of gatekeeping device 14, for example, such that only patient 14 can operate gatekeeping device 14. After gatekeeping device 14 is associated with patient 10, method 32 proceeds to step 36, where communications software is received by and installed into gatekeeping device 14. Such communications software supports communications, encoding, validation of authorization, and other operations used to facilitate communications between implantable biomedical device 10 and remote authorized entities via the internet.

After such configuring of gatekeeping device 14, method 32 proceeds to step 38, where the processor of gatekeeping device 14 determines location of gatekeeping device (e.g., via a GPS location system. Then at step 40, processor 36 compares the location determined with an authorized location or with a plurality of authorized locations for pairing gatekeeping device 14 with implantable biomedical device 10. If, at step 40, the location determined does not corresponds to the authorized location or locations for pairing, then method 32 ends. If, however, at step 40, the location determined does correspond to the authorized location or locations for pairing, then at step 42, gatekeeping device 14 transmits a Media Access Control (MAC) address to implantable biomedical device 10. The MAC address transmitted to implantable biomedical device 10 corresponds to the communications channel used by gatekeeping device 14 for communications with implantable biomedical device 10.

Method 32 then proceeds to step 44, where gatekeeping device 14 receives a unique identifier associated with implantable biomedical device 10. Such a unique identifier can be broadcast by implantable biomedical device 12 of can be provided by the manufacturer, physician, or hospital. For example, such a unique identifier can be transmitted by implantable biomedical device 10 in response to receiving the MAC address of gatekeeping device 14. In some embodiments, such a unique identifier can be manually keyed into gatekeeping device 14 or can be transmitted to gatekeeping device 14 over a communications channel from some other source (e.g., personal computer 24 used by physician 28). Method 32 then proceeds to step 46, where gatekeeping device is provided with data pertaining to IP-addressable website 26 corresponding to implantable biomedical device 12. Then, at step 48, gatekeeping device communicates with IP-addressable website. Gatekeeping device 14, for example, will communicate using a public/private encoding algorithm. Gatekeeping device 14 might send IP-addressable website 26 information pertaining to gatekeeping device 14, so that IP-addressable website 26 can validate that gatekeeping device 14 is authorized to communicate with IP-addressable website 26. Gatekeeping device 14 is now configured to provide gatekeeping function for communications between IP-addressable website 46 and implantable biomedical device 12, and so method 32 ends.

Figure 3:
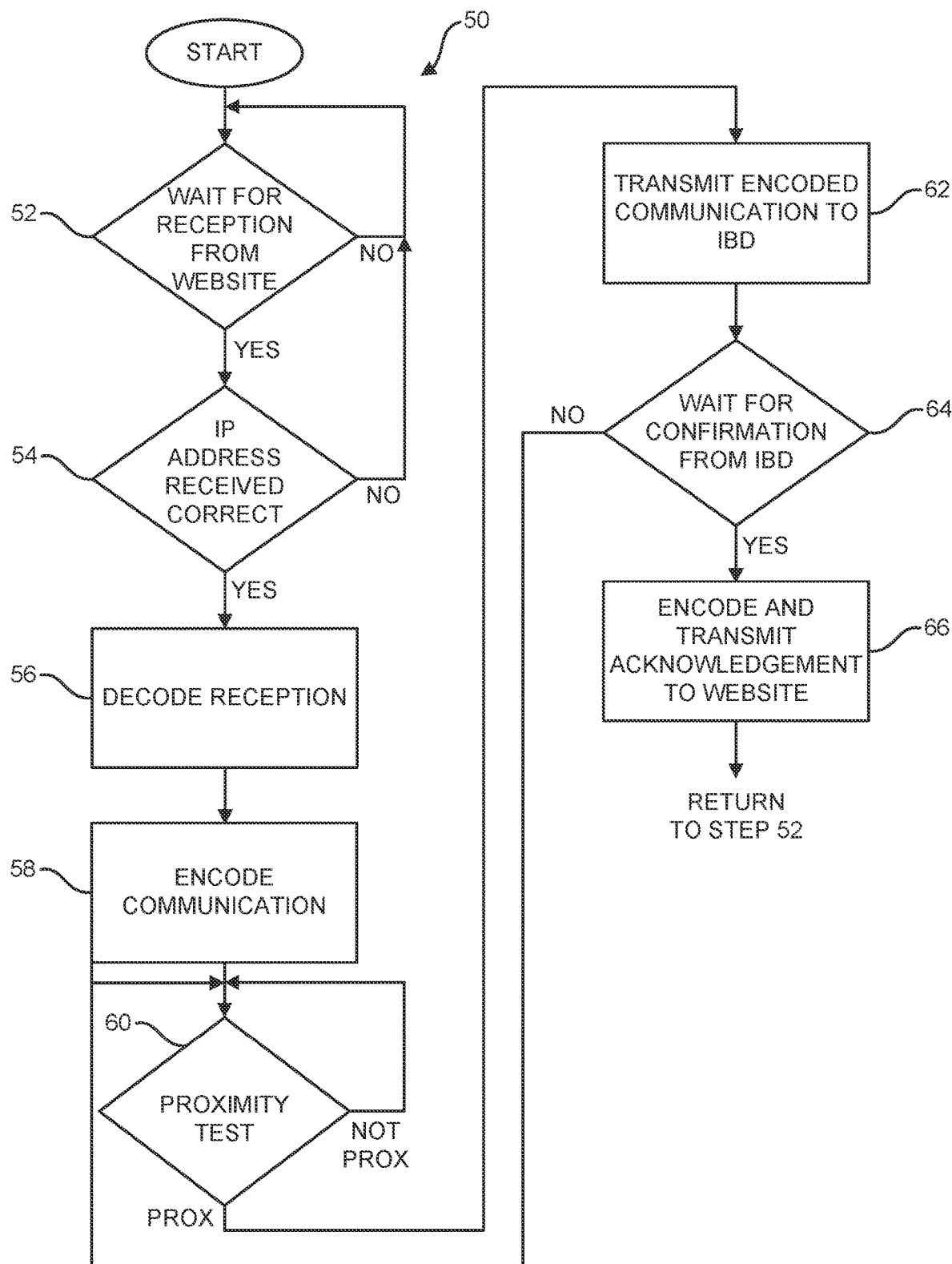
FIG. 3 is a flow chart of a method for providing secure gatekeeping of communications from an implantable biomedical device to a remote internet-based website.
Figure 4:
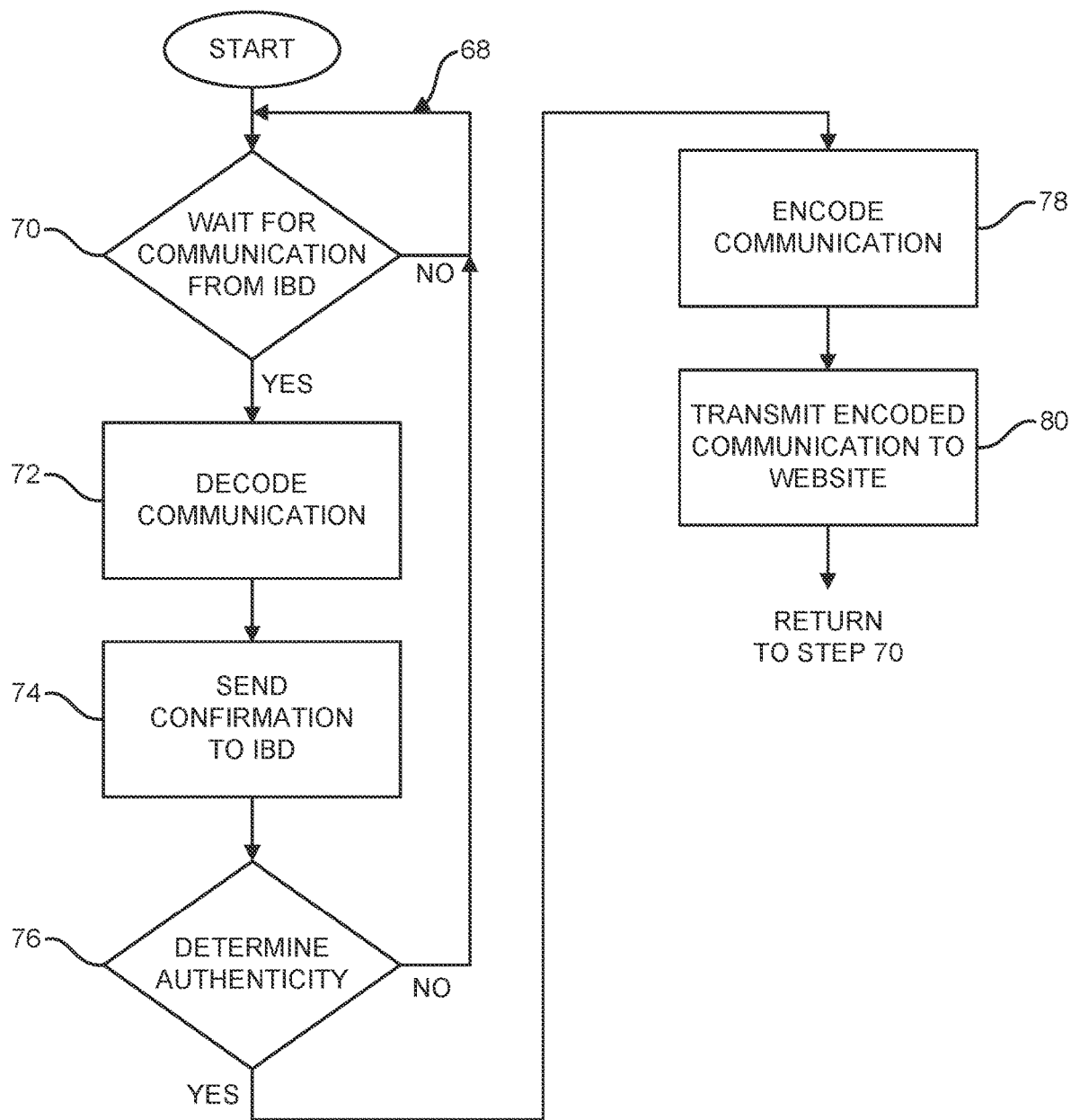
FIG. 4 is a flow chart of a method for providing secure gatekeeping of communications from a remote internet-based website to an implantable biomedical device.
Figure 5:
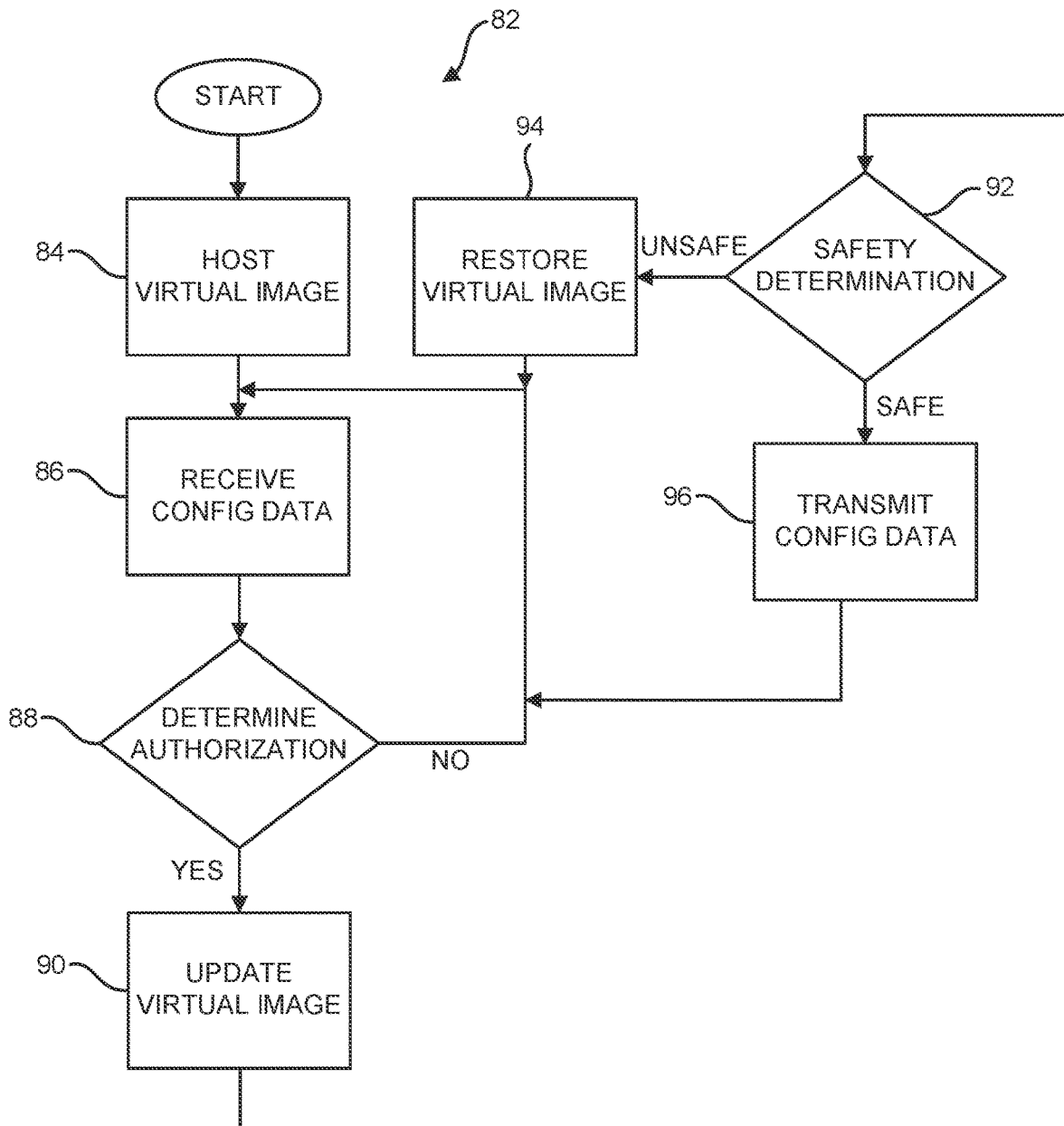
FIG. 5 is a flow chart of a method for facilitating a remote internet-connected device to configure an implantable biomedical device.

FIGS. 3-6 will describe communication methods used for communications between implantable medical device 12, as depicted in FIG. 1, with various authorized users. In FIGS. 3-4, communication methods of gatekeeping device 14 will be described. In FIG. 5, a method for facilitating a remote internet-connected device to configure an implantable biomedical device will be described.

FIG. 3 is a flow chart of a method for providing secure gatekeeping of communications from an implantable biomedical device to a remote internet-based website. In FIG. 3, method 50 is described from a vantage point of a processor of gatekeeping device 14 (depicted in FIG. 1). Method 50 begins at step 52, where gatekeeping device 14 waits to receive a communication from internet-based websites. If, at step 52, no communication is received from a remote internet-based website, then method 50 remains (or returns to) step 52. If, however, at step 52, gatekeeping device 14 receives a communication from a remote internet-based website, then gatekeeping device 14 proceeds to step 54.

At step 54, gatekeeping device 14 compares an IP address corresponding to the communication received with an IP address corresponding to IP-addressable website 26, which is the website that corresponds to implantable medical device 12. If, at step 54, gatekeeping device 14 determines that the communication received is from an IP address that does not correspond to IP-addressable website 26, then method 50 returns to step 52 and awaits another internet-based communication. If, however, at step 54, gatekeeping device 14 determines that the communication received is from an IP address that does correspond to IP-addressable website 26, then method 50 proceeds to step 56.

At step 56, gatekeeping device decodes the communication received using a public key transmitted therewith by IP-addressable website 26 and private key of gatekeeping device 14. Using such public and private keys to decode the communication ensures that the communication has originated by IP-addressable website 26 and is intended for reception by gatekeeping device 14. Then at step 58, gatekeeping device 14 encodes the communication decoded in accordance with an encryption algorithm used by implantable biomedical device 10. Then, at step 60, gatekeeping device performs a proximity test. The proximity test is to determine if gatekeeping device 14 is within a predetermined distance from implantable medical device 10. Such proximity test is described below. If, at step 60, gatekeeping device determines that gatekeeping device is not proximate implantable biomedical device 12, then method 50 remains at step 60 until gatekeeping device 14 determines that it is proximate implantable medical device 12. If, however, at step 60, gatekeeping device determines that gatekeeping device is proximate implantable biomedical device 12, then method 50 proceeds to step 62.

At step 62, gatekeeping device 14 transmits the encoded communication to implantable medical device 12. Then method 50 proceeds to step 64, where gatekeeping device 14 waits for a confirmation communication from implantable medical device 12. If at step 64, gatekeeping device 14 has not received a confirmation communication from implantable medical device 12 within a predetermined time frame, method 50 returns to step 60, where gatekeeping device 14 again performs a proximity test. If, however, at step 64, gatekeeping device 14 has received a confirmation communication from implantable medical device 12 within a predetermined time frame, method 50 proceeds to step 66, where gatekeeping device 14 encodes and transmits an acknowledgement communication to IP-addressable website 26. Then method 50 returns to step 52 and awaits another communication from internet-based websites.

FIG. 4 is a flow chart of a method for providing secure gatekeeping of communications from a remote internet-based website to an implantable biomedical device. In FIG. 4, method 68 is described from a vantage point of a processor of gatekeeping device 14 (depicted in FIG. 1). Method 68 begins at step 70, where gatekeeping device 14 waits to receive a communication from implantable medical device 12. If, at step 70, no communication is received from implantable medical device 12, then method 68 remains (or returns to) step 70. If, however, at step 70, gatekeeping device 14 receives a communication from implantable medical device 12, then gatekeeping device 14 proceeds to step 72.

At step 72, gatekeeping device 14 decodes the communication received from implantable biomedical device 12. Then, at step 74, gatekeeping device 14 sends a confirmation communication to implantable biomedical device 12. Method 68 then proceeds to step 76, where gatekeeping device determines authenticity that the communication received was transmitted by implantable biomedical device 12. Such determination of authenticity will be described in more detail below. If, at step 76, the authenticity of the communication received is not determined, method 68 returns to step 70 and awaits another communication. If, however, at step 76, the authenticity of the communication received is determined, then method 68 proceeds to step 78, where gatekeeping device 14 encodes the communication decoded, using an encoding algorithm used for communications between gatekeeping device 14 and IP-addressable website 26. Then, at step 80, gatekeeping device transmits the encoded communication to IP-addressable website 26. Method 68 then returns to step 70, where gatekeeping device awaits another communication transmitted by implantable biomedical device 12.

FIG. 5 is a flow chart of a method for facilitating a remote internet-connected device to configure an implantable biomedical device. In FIG. 5, method 82 is described from a vantage point of a processor of hosting server 20 (depicted in FIG. 1), which hosts IP-addressable internet site 26. Method 82 begins at step 84, where hosting server 20 hosts virtual image 30 of implantable biomedical device 12 at IP-addressable internet site 26 associated therewith. Such virtual image 30 of implantable biomedical device 12 can be configured to behave or operate identically to the corresponding actual implantable biomedical device 12. Then, method 82 proceeds to step 86, where IP-addressable internet site 26 receives, from the remote internet-connected device via the internet, configuration data for implantable biomedical device 12 at IP-addressable internet site 26. Then, at step 88, hosting computer 20 determines authorization of a remote entity transmitting the configuration data from the remote internet-connected device. If, authorization has not been determined at step 88, method 82 returns to step 86 and waits to receive another communication containing configuration data for implantable biomedical device 12.

If, however, at step 88, authorization has been determined at step 88, method 82 proceeds to step 90, where hosting server 20 updates virtual image 30. Method 82 then proceeds to step 92, where safety of implantable biomedical device 12 is determined. Safety is determined based on virtual image 30 as updated. In some embodiments, simulations of virtual image 30 is performed. Such a safety determination can include a determination of directional safety—Is the safety improved or impaired by such an update? In some embodiments, the update will be permitted in the actual implantable biomedical device 12, only if the directional safety is improved. In some embodiments a waiting time period is required following an update before the update is permitted to be performed on the actual implantable biomedical device 10. If, at step 92, the safety requirements of the update have not been met, method 82 proceeds to step 94, where hosting server 20 restores virtual image 30 to its pre-update configuration, and then method 82 returns to step 86.

If, however, at step 92, the safety requirements of the update have not been met, method 82 proceeds to step 96, where hosting server 20 transmits, from IP-addressable internet site 26 via the internet to implantable biomedical device 12. Such transmission is encoded via an encryption method used for transmissions between IP-addressable internet site 26 and gatekeeping device 14, which serves as a gatekeeper for all communications with implantable biomedical device 12. Method 82 then returns to step 86, where it awaits reception of another communication from a remote internet-connected device.

The various encoding, authorization, validation, and other security measures described in the methods corresponding to FIGS. 2-5 will be described in more detail below. Various embodiments will use more or fewer steps in one or all of methods 32, 50, 68 and 82 described above. These methods above describe example embodiments of the gatekeeping function of gatekeeping device 14 and of the hosting server 20. Gatekeeping device 14, ensures that only authorized entities can send data (e.g., configuration data) to implantable biomedical device 12. Similarly, gatekeeping device 14 relays communications received from implantable biomedical device 12 only if gatekeeping device can determine that such communications were transmitted by implantable biomedical device 12. Hosting server 20 ensures safety of configuration updates and limits communications to implantable biomedical device therefrom.

Proximal Pairing

Proximal pairing can be used to provide a high level of security by requiring some or all communications between implantable biomedical device 12 and a remote authorized entity to be conducted through gatekeeping device 14 that is proximate and paired with implantable biomedical device 12. Gatekeeping device 14 can provide security to communications by restricting communications to and from implantable biomedical device 12 to only a paired (i.e., paired with the implantable biomedical device) device that is proximate implantable biomedical device 12 and which has been authorized to conduct such communications therewith. Only such a configured and authorized device can facilitate these communications between implantable biomedical device 12 and remote authorized entities, and then only if the configured and authorized device is proximate implantable biomedical device 12. Implantable biomedical device 12 can be configured to have a limited range of wireless communication with the paired proximate device, such as, for example, gatekeeping device 14. In this way, such a paired proximate device can operate as a gatekeeper for communications to and/or from implantable biomedical device 12 to which it is paired. By requiring communications to be relayed by such a paired proximate device, such a gatekeeping role can thwart attempted communications to and/or from implantable biomedical device 12 that are not conducted by authorized remote entities.

Various types of devices can be paired with implantable biomedical device 12. For example, a manufacturer of implantable biomedical device 12 might provide a complementary pairing device specifically designed for such a gatekeeping role. Exemplary pairing operations for such gatekeeping devices will be described below. In some embodiments, a cell phone of patient 10 can be configured to perform these gatekeeping operations. In various embodiments, communication between implantable biomedical device 12 and the paired proximate device can be conducted using various protocols. For example, any protocol conducive to short-range communications between a proximate device and a subcutaneous implantable biomedical device can be used. Some such communications protocols include Bluetooth, Zigbee, Near-Field Communication (NFC), Wide-Field Communication (WiFi), etc. These various communications protocols can be used in various manners to ensure fast and securing pairing of and communicating between an implantable biomedical device and a proximate device. For example, in some embodiments, NFC communications can initiate Bluetooth pairing, for example.

Various ways of proximal pairing of implantable biomedical device 12 with a gatekeeping device, such as gatekeeping device 14, can be performed, and various limits to the number of paired devices can be established. For example, a limit of a single, or two, or a limited few number of devices can be paired with a specific implantable biomedical device. This one or these few devices can be paired in a secure manner that precludes invasive pairings of other devices by unauthorized entities. Such secure pairing can be accomplished using various secure pairing protocols. For example, implantable biomedical device 12 can be configured to be paired in limited and/or controlled conditions. Such limited and/or controlled conditions can include limiting the times when pairings are performed, limiting locations where pairings are performed, authorizing pairings using a pairing-authorization device, and/or by using secure communications between implantable biomedical device 12 and the device to which it is to be paired (as well as any pairing-authorization device).

The times, during which pairing is permitted to occur, can be limited in various manners. For example, pairing of implantable biomedical device 12 to gatekeeping device 14 can be limited to the time of implantation of the implantable biomedical device. Other permitted times for pairing of implantable biomedical device 12 can be limited to times at which certain other events take place. For example, during hospital visits and/or doctors' appointments, pairing can be permitted to be performed. Devices can be paired in such circumstances as hospital visits and/or doctors' appointments using a doctor's pairing key and/or a pairing-authorization device, for example. Pairing can be authorized upon receipt of a doctor's pairing key, which can be a software key or a hardware key, for example. The key can be communicated to gatekeeping device 14, thereby permitting pairing to commence.

The locations where pairings are permitted can be limited in various ways. For example, the pairings can be limited using a GPS location sensor contained in a proximate device to be paired with implantable biomedical device 12. A predetermined number of locations where pairing is permitted can be compared with the location as sensed by the GPS location sensor of the proximate device to be paired. For example, the home address of patient 10 in whom implantable biomedical device 12 has been implanted can be a permissible location where pairing can be performed. Other permissible pairing locations can include locations of the manufacturer of implantable biomedical device 12, locations of the doctors' offices where treatment patient 10 who has implantable biomedical device 12 are conducted, and/or locations of hospitals where implantation of the such implantable biomedical devices are performed.

In some embodiments the security of proximal pairing communications can be further bolstered using proximity sensing and/or proximity testing. For example, proximity between implantable biomedical device 12 and the gatekeeping device 14 can be sensed using a proximity sensor. This proximity sensor can sense relative proximity of implantable biomedical device 12 to gatekeeping device 14. Communications to and/or from implantable biomedical device 12 can be enabled only when such relative proximity of implantable biomedical device 12 to gatekeeping device 14 meets a threshold condition. For example, if gatekeeping device 14 is within a predetermined distance from implantable biomedical device 12, communications therebetween could be enabled. Various types of proximity sensors can be employed for such a purpose. For example, implantable biomedical device 12 could have a reed switch configured to sense a magnetic field generated by a magnet or by a magnetic field generated by an inductive coil of gatekeeping device 14. In other embodiments, a signal strength of an attempted wireless communication can be compared with a predetermined threshold so as to determine if gatekeeping device 14 is within a predetermined distance of implantable biomedical device 12.

In some embodiments, pairing can occur as follows. Before implantable biomedical device 12 is implanted, it is paired with gatekeeping device 14. Gatekeeping device 14 is equipped with a gatekeeping app that has been programmed by the manufacturer of implantable biomedical device 14. The gatekeeping app is configured to provide secret encryption and decryption of communications between gatekeeping device 14 and implantable biomedical device 12. For example, in some embodiments, implantable biomedical device uses a secret encryption method that is based on a running timer that commences upon the first powering of implantable biomedical device 12. Every minute, the counter advances and the encryption changes based upon that advanced count. Gatekeeping device 14 is provided with the time of first power up during this pairing operation, and gatekeeping device 14 synchronizes a counter to the counter of implantable biomedical device 12. Gatekeeping device 14 is in this way able to encrypt and decrypt communications in synchrony with implantable biomedical device 12.

Directional Safety

Directional safety is a term indicative of whether safety in increased or decreased by a change in the configuration or programming of a device, such as an implantable biomedical device. In the context of an implantable biomedical device, the safety to which the term "direction safety" refers is the safety of the patient in whom the implantable biomedical device has been implanted. Some updates to an implantable device might not improve safety, but a physician of the patient might desire such an update in spite of its negative directional safety. Such an update can be performed in various secure fashions. For example, if a physician desires to update and/or reconfigure an implantable device in a manner having neutral or negative directional safety, such updates and reconfigurations can be restricted to local settings. Distal internet communications can be prohibited from performing such neutral or negative directional-safety updates and/or reconfigurations.

Furthermore, devices that communicate such neutral or negative directional-safety updates and/or reconfigurations can be restricted to special devices manufactured by the manufacturer of the implantable device. Secret encoding schemes can be used for such communications of neutral or negative directional-safety updates. Proximity requirements between the programming device and the implantable biomedical device can be required, so as to ensure that only local secure communications perform such neutral or negative directional-security updates and/or reconfigurations.

In some embodiments, any change to firmware of an implantable biomedical device can be considered to have a negative directional safety (or at least a non-insignificant potential for negative directional safety). Such firmware changes can be restricted to such local secure communications methods as other neutral or negative directional-safety updates and reconfigurations.

Communication Encryption

Data encryption for communications between implantable biomedical device 12 and the remote entity and/or between various intermediate devices facilitating such communications can be performed. For example, a relatively simple encryption can be performed for communications between implantable biomedical device 12 and gatekeeping device 14, so as to enable low-power operation of implantable biomedical device 12. In some embodiments, communications between implantable biomedical device 12 and gatekeeping device 14 can be encrypted by an encryption method that is secret—devised but unpublished by the manufacturer. Such a secret encryption method can make use of the Machine Access Control (MAC) address of the communicating device(s), such as for example a Bluetooth chip. Furthermore, a clock algorithm can be used to encrypt such proximate communications such that knowledge of the MAC address is insufficient to break the code.

More power-hungry encryption methods can be used for devices that have higher power budgets, such as gatekeeping device 14 and enterprise devices, such as hosting server 20, conducting internet-based operations. Various such encryption methods can be used for communications between such higher-power-budget devices. For example, public/private key encryption can be used for communications between gatekeeping device 14 and internet-based servers, such as hosting server 20.

In some embodiments, such public keys can be exchanged once or at various intervals. For example, a new private key can be generated by the paired proximate device every new day, new hour, or at five-minute intervals, for communications conducted by gatekeeping device 14 and remote internet-based servers. Gatekeeping device 14 can then generate a public key based on the private key generated. This public key can be communicated to the remote internet-based server, such as hosting server 20, for use in decoding communications originated by gatekeeping device 14. Similarly, the remote internet-based server can also generate a private/public key combination and transmit the public key to gatekeeping device 14. Such frequent changing of these private/public key combinations can limit the time for a hacker to hack the private key to one day or less—a small fraction of the time required for such hacking for today's most powerful computers.

Device Authentication

A proximate device that is to be paired with implantable biomedical device 12 can communicate therewith using an authentication protocol. Such authentication can be performed via various secure authentication methods. For example, at the time of implantation, implantable biomedical device 12 can be associated with patient 10 via secure registration of implantable biomedical device 12 at a secure internet sight of the manufacturer. The registration procedure can include providing the manufacturer with information regarding patient 10 as well as a serial number of the implantable biomedical device 12, for example. In some embodiments, the manufacturer's website can request a login ID and password be supplied for patient 10. The manufacturer's website can request information regarding the implantable biomedical device 12 and/or devices to be paired with implantable biomedical device 12, such as, for example, gatekeeping device 14.

In some embodiments, after or during the collection of information pertaining to patient 10 and/or implantable biomedical device 12, the manufacturer can communicate with gatekeeping device 14, which is to be paired with implantable biomedical device 12. Such a communication can occur in various manners. For example, if gatekeeping device 14 is a cellphone, the manufacture can send a text message or a voice message to the cellphone. In other embodiments the manufacturer can display a key code for the user to use during the pairing procedure. For example, the manufacturer can display a key code that the patient inputs into the device to be paired. The key code then enables the pairing of the proximate device to implantable biomedical device 12. In some embodiments, the manufacturer can maintain a log of all the devices that are and/or have been paired with implantable biomedical device 12.

In some embodiments, a time synchronized code can be used for authentication and/or encryption purposes. A time sequence of codes can be synchronized at a time of implantation and/or pairing, for example. The code sequence can be synchronized between the communicating devices, such that the code communicated at a given time of communication can be anticipated by the device to which the code is communicated (e.g., implantable biomedical device 12, gatekeeping device 14, and/or hosting server 20).

Virtual Image (Mirrored Counterpart of Implantable Biomedical Device)

Communication between an authorized entity can be performed either indirectly, using virtual image 30 that is a mirrored counterpart to implantable biomedical device 12, or directly, without such a virtual image. For example, programming updates to implantable biomedical device 12 can be required to be performed first on virtual image 30. A doctor, for example, might want to change a therapy schedule that implantable biomedical device 12 performs for patient 10. This change in the therapy schedule might have been in response to sensed biometric data indicative of condition of patient 10, what has been provided by implantable biomedical device 12. Virtual image 30 can then transmit the updated therapy schedule to implantable biomedical device 12 if the updated therapy schedule has been determined to meet certain safety requirements.

Virtual image 30 can mirror the actual implantable biometric device 12, such that simulations of the behavior of virtual image 30 can be indicative of the performance of the actual implantable biometric device 12, after such updated therapy schedule has been programmed. Because any programming changes are made first to virtual image 30, all such programming changes can be vetted so as to ensure that such programming changes, when made to the actual implantable biomedical device 12, will be safe for patient 10, in whom the actual implantable biomedical device 12 has been implanted. Virtual image 30 is managed at an IP addressable website by hosting computer 20. Hosting computer 20 is not power limited, and therefore can have any processing power that is needed to perform its duties. In one embodiment, hosting computer 20 can be an enterprise computer.

Such an enterprise computer, as is typically used for performing such simulations, has good computational power so as to be able good performance of complex algorithms, such as, for example, simulations of implantable biomedical device 12 configured in various manners. These simulations can be used to determine directional safety of any updates and/or reconfigurations to implantable biomedical device 12. The enterprise computer can then act as a mediator for potential updates and/or reconfigurations of implantable biomedical device 12. For example, the enterprise computer can accept or reject such potential changes based on the determined directional safety, which in turn is based on the virtual simulations of virtual image 30 as virtually updated with such potential updates and/or reconfigurations.

Hosting computer 20 can be configured to perform simulations on implantable biomedical devices for a great many patients. For example, if a manufacturer wants to upgrade the firmware of all implantable biomedical devices of a specific type, hosting computer 20 can run simulations based on all of the virtual devices corresponding to the implantable biomedical device implanted in these patients. Based on such a multitude of simulations, the manufacturer can decide whether or not to proceed with such updated firmware across the entire population of implantable biomedical devices.

Operation without a Gatekeeping Device

In some embodiments, secure communications can be performed directly between implantable biomedical device 12 and internet cloud 16. For example, implantable biomedical device 12 can be configured to communication directly with internet cloud 16 via 4G or 5G cell-phone communications protocols. In such systems, communications to and from implantable biomedical device 12 can be restricted to those with IP addressable website 26. Static IP addresses of implantable biomedical device 12 and IP addressable website 26 can be secret so as to operate as a paired set only between which communications are permitted. To provide further security to such direct communications between implantable biomedical device 12 and IP addressable website 26, public/private key encryption can be used.

Direct communications between implantable biomedical device 12 and IP addressable website 26 can incur a power cost that might be greater than the power cost associated with indirect communication via gatekeeping device 14. Such power costs can be provided by rechargeable batteries that perform any therapeutic functions of implantable biomedical device 12 as well as providing such direct communications. Because the therapeutic function of implantable biomedical device 12 should not be interrupted, power provided for therapeutic function should not be interrupted. To ensure continuous power provision for therapeutic function, some embodiments have separate batteries, one for providing power for therapeutic function, and another for conducting communications. In other embodiments, a single rechargeable battery can be virtually partitioned such that a first battery partition is reserved for providing power for therapeutic function, and second battery partition is reserved for conducting communications. If, for example, the second battery partition is depleted and a communication is scheduled, the scheduled communication can be rescheduled to a later time window, so as to reserve the energy stored in the first battery partition for providing power for therapeutic function.

To further reduce power required for such direct communications, these direct communications can be limited to limited time windows. For example, implantable biomedical device 12 can wake up a receiver for a short duration time window every five minutes to determine if IP addressable website 26 is transmitting a communication thereto or to transmit a communication to IP addressable website 26. IP addressable website 26 can maintain the schedule for such communications so as to synchronize transmissions and receptions with implantable biomedical device 12.

Other power saving measures can also facilitate such direct communications. For example, for implantable biomedical devices that are implanted deep within patient 10, a communications antenna of such deeply implanted biomedical devices can be subcutaneously situated just beneath a skin layer of the patient. Such situation of the communications antenna can permit lower power requirements for a given signal strength than would be required for a more deeply implanted antenna. Such antenna configurations are disclosed in U.S. patent application Ser. No. 16/355,236, entitled "Subcutaneous Device for Monitoring and/or Providing Therapies," by Yatheendhar D. Manicka, filed Mar. 15, 2019, which is hereby incorporated by reference in its entirety.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method for facilitating a remote internet-connected device to configure an implantable biomedical device, the method comprising:

hosting a virtual image of the implantable biomedical device at an IP-addressable internet site associated therewith;

receiving, by the IP-addressable internet site and from the remote internet-connected device via the internet, configuration data for the implantable biomedical device;

updating the virtual image hosted based on the configuration data received;

determining whether directional safety of the implantable biomedical device would be increased upon updating the implantable biomedical device with the configuration data based on simulations of the virtual image as updated;

advancing a counter every minute following the time at which Implanted medical device was first powered;

encoding the configuration data based on the counter; and transmitting, from the IP-addressable internet site via the internet to the implantable biomedical device, the encoded configuration data, in response to the directional safety of the implantable biomedical device determined to be increased.

2. The method of claim 1, wherein transmitting the configuration data comprises:

transmitting, from the IP-addressable internet site via the internet to a gatekeeping device, the configuration data, in response to the configuration data being validated; and wirelessly transmitting, from the gatekeeping device to the implantable biomedical device if the gatekeeping device is within a predetermined range of the implantable biomedical device, the configuration data received.

3. The method of claim 2, wherein the predetermined range is determined by a range limit of reed switch activation in the implantable biomedical device by a magnetic field generated by the gatekeeping device.

4. The method of claim 2, wherein the predetermined range is determined by a range limit of Near Field Communication (NFC) between the implantable biomedical device by a magnetic field generated by the gatekeeping device.

5. The method of claim 2, wherein the predetermined range is determined by a range limit of Bluetooth communication between the implantable biomedical device by a magnetic field generated by the gatekeeping device.

6. The method of claim 1, wherein
the configuration data is encoded using public/private key encoding based on a public key corresponding to a provided by the gatekeeping device and further based on a private key corresponding to a provided by the IP-addressable internet site.

7. The method of claim 1, further comprising:
determining authorization of a remote entity transmitting the configuration data from the remote internet-connected device,
wherein updating the virtual image hosted is contingent upon the authorization of the remote entity determined.

8. The method of claim 1, wherein the configuration data is not transmitted, from the IP-addressable internet site via the internet to the implantable biomedical device, in response to the safety of the implantable biomedical device determined to be neutral or negative.

9. A system for facilitating a remote internet-connected device to configure an implantable biomedical device, the system comprising:
a hosting computer in communication with the internet; and
computer readable memory encoded with instructions that cause the system to:
host a virtual image of the implantable biomedical device at an IP-addressable internet site associated therewith;
receive, by the IP-addressable internet site and from the remote internet-connected device via the internet, configuration data for the implantable biomedical;
update the virtual image hosted based on the configuration data received;
determine whether directional safety of the implantable biomedical device would be increased upon updating the implantable biomedical device with the configuration data based on simulations of the virtual image as updated;

advance a counter every minute following the time at which Implanted medical device was first powered;
encode the configuration data based on the counter; and
transmit, from the IP-addressable internet site via the internet to the implantable biomedical device, the configuration data in response to the directional safety of the implantable biomedical device being determined to be increased.

10. The system of claim 9, wherein transmitting the configuration data comprises:
transmitting, from the IP-addressable internet site via the internet to a gatekeeping device, the configuration data, in response to the configuration data being validated; and
transmitting, from the gatekeeping device to the implantable biomedical device if the gatekeeping device is within a predetermined range of the implantable biomedical device, the configuration data received.

11. The system of claim 10, wherein the predetermined range is determined by a range limit of reed switch activation in the implantable biomedical device by a magnetic field generated by the gatekeeping device.

12. The system of claim 10, wherein the predetermined range is determined by a range limit of Near Field Communication (NFC) between the implantable biomedical device by a magnetic field generated by the gatekeeping device.

13. The system of claim 10, wherein the predetermined range is determined by a range limit of Bluetooth communication between the implantable biomedical device by a magnetic field generated by the gatekeeping device.

14. The system of claim 9, wherein:
the configuration data is encoded using public/private key encoding based on a public key corresponding to a provided by the gatekeeping device and further based on a private key corresponding to a provided by the IP-addressable internet site.

15. The system of claim 9, further comprising:
determining authorization of a remote entity transmitting the configuration data from the remote internet-connected device,
wherein updating the virtual image hosted is contingent upon the authorization of the remote entity determined.

16. The system of claim 9, wherein the configuration data is not transmitted, from the IP-addressable internet site via the internet to the implantable biomedical device, in response to the directional safety being determined to be neutral or negative.

* * * * *